(12) United States Patent
Tokuyasu et al.

(10) Patent No.: US 7,728,180 B2
(45) Date of Patent: Jun. 1, 2010

(54) METHOD FOR PRODUCING ETHERS

(75) Inventors: Jin Tokuyasu, Kurashiki (JP); Taketoshi Okuno, Kurashiki (JP); Takashi Hori, Kurashiki (JP); Hideharu Iwasaki, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 433 days.

(21) Appl. No.: 11/628,865

(22) PCT Filed: Jun. 8, 2005

(86) PCT No.: PCT/JP2005/010504

§ 371 (c)(1),
(2), (4) Date: Jan. 25, 2008

(87) PCT Pub. No.: WO2005/121059

PCT Pub. Date: Dec. 22, 2005

(65) Prior Publication Data

US 2008/0262272 A1    Oct. 23, 2008

(30) Foreign Application Priority Data

Jun. 11, 2004    (JP) .............................. 2004-174208

(51) Int. Cl.
*C07C 41/06*    (2006.01)
(52) U.S. Cl. .................. 568/690; 568/687; 568/689
(58) Field of Classification Search ............... None
See application file for complete search history.

(56) References Cited

U.S. PATENT DOCUMENTS

| 3,670,029 | A | 6/1972 | Romanelli |
|---|---|---|---|
| 3,670,032 | A | 6/1972 | Romanelli |
| 3,769,352 | A | 10/1973 | Romanelli |
| 3,780,074 | A | 12/1973 | Romanelli |
| 3,887,627 | A | 6/1975 | Romanelli |
| 2005/0038273 | A1 | 2/2005 | Rottger et al. |

FOREIGN PATENT DOCUMENTS

| JP | 48 43327 | 12/1973 |
|---|---|---|
| JP | 2003 334450 | 11/2003 |
| JP | 2004 137237 | 5/2004 |
| JP | 2004-534059 | 11/2004 |
| JP | 2005-95850 | 4/2005 |
| WO | WO 02/100803 A2 | 12/2002 |
| WO | WO 2004/065006 A1 | 8/2004 |

OTHER PUBLICATIONS

Wolfgang A. Herrmann, "N-Heterocyclic Carbenes: A New Concept in Organometallic Catalysis", Angew. Chem. Int. Ed., vol. 41, 2002, pp. 1290-1309.
Jiro Tsuji, Palladium Reagents and Catalysts, Innovations in Organic Synthesis, 1995, 2 cover pages and pp. 423-449.

*Primary Examiner*—Rosalynd Keys
(74) *Attorney, Agent, or Firm*—Oblon, Spivak, McClelland, Maier & Neustadt, L.L.P.

(57) ABSTRACT

A method for producing ethers comprises the following steps:

initiating telomerization process of a conjugated diene compound with an hydroxyl compound represented by the following formula (I):

$$R^1OH \qquad (I)$$

in the presence of a palladium compound, a tertiary isocyanide represented by the following formula (II):

$$R^2NC \qquad (II),$$

and a base; and adding halfway through the telomerization process a tertiary phosphine represented by the following formula (III):

$$PR^3R^4R^5 \qquad (III)$$

(the respective symbols are defined in the description).

5 Claims, No Drawings

METHOD FOR PRODUCING ETHERS

TECHNICAL FIELD

The present invention relates to a method for producing ethers by the telomerization using conjugated diene compounds. Ethers produced by the method of the present invention are useful as raw materials in the production of polymers and intermediates of perfumes and so on.

BACKGROUND ART

Telomerization using conjugated diene compounds is a process in which a conjugated diene compound incorporates an nucleophilic reactants, such as an alcohol, to form an oligomer. For example, two molecules of 1,3-butadiene react with one molecule of a compound containing an active hydrogen, such as acetic acid, to form 1-acetoxy-2,7-octadiene. In telomerization process, a palladium compound, especially one coordinated with a phosphine, serves as an effective catalyst (See Non-Patent Documents 1 and 2).

Moreover, the telomerization process is reported that a catalyst comprising a tertiary phosphine or an isocyanide, and a nickel compound is used (See Patent Document 1). And the telomerization process is reported that a palladium carbene complex is used in the presence of a base (See Patent Document 2). Other known telomerization processes are reported that a catalyst comprising a primary isocyanide and tetrakis(triphenylphosphine)palladium is used (See Patent Document 3), and one that uses a catalyst comprising a tertiary isocyanide and a palladium compound (See Patent Document 4).

Non-Patent Document 1: Tsuji, Jiro. *Palladium Reagents and Catalysts*. John Wiley & Sons, (1995): pp. 423-441.

Non-Patent Document 2: *Angew. Chem. Int. Ed.*, Vol. 41 (2002): pp. 1290-1309.

Patent Document 1: U.S. Pat. No. 3,670,029

Patent Document 2: Published Japanese Translation of PCT International Application No. 2004-534059

Patent Document 3: Japanese Patent Publication No. Sho 48-43327 (see Example 9)

Patent Document 4: Japanese Patent Laid-Open Publication No. 2005-95850

DISCLOSURE OF THE INVENTION

Problems to be Solved by the Invention

The palladium catalysts used in the processes described in Non-Patent Documents 1 and 2 are difficult to be recycled and make the processes costly. This is because the catalysts, coordinated with a phosphine, have a low stability against heat and tend to decompose to form palladium black when the reaction products are separated from the catalyst by evaporation upon completion of the reaction.

The process described in Patent Document 1 has a high selectivity for the by-products (About 10 to 30%), and requires a large amount of catalyst because of the low catalytic activity. The process thus is not an effective approach to produce ethers.

The catalyst used in the process described in Patent Document 2 is formed of a nitrogen-containing heterocyclic carbene coordinated with a palladium compound and requires the base to be added in large excess of the catalyst to increase the efficiency of the reaction. However, the presence of the excess base causes corrosion of the reactor and clogging of the piping and makes the catalyst unstable.

In the process described in Patent Document 3, the palladium compound coordinated with a phosphine is used. This prevents the coordination of the isocyanide to the palladium atom. As a result, the reaction is significantly slowed and the selectivity for the desired product is decreased, as is the yield of the desired product (approx. 17%). The process therefore is not suitable for industrial production of ethers. The present inventors have also confirmed that when crude butadiene, a cost-effective low-purity industrial material comprising 1,3-butadiene (approx. 40 wt %) and impurities such as butenes (e.g., isobutylene), acetylenes (e.g., methylacetylene and 1-buthyne) and 1,2-butadiene, is used as the starting material in the process of Patent Document 4, the reaction rate is significantly decreased. Thus, the process described in Patent Document 4 still needs to be improved to realize the efficient and cost-effective industrial production of ethers.

It is therefore an object of the present invention to provide an industrially advantageous method for producing ethers that can use even low-purity, less costly conjugated diene compounds to achieve high conversion and selectivity.

Means for Solving the Problems

The above-described object of the present invention can be achieved by a method for producing an ether, comprising the steps of:

initiating telomerization process of a conjugated diene compound with an hydroxyl compound represented by the following formula (I):

$$R^1OH \qquad (I),$$

wherein $R^1$ is a substituted or unsubstituted alkyl or aryl group (the compound is referred to as hydroxyl compound (I), hereinafter), in the presence of a palladium compound, a tertiary isocyanide represented by the following formula (II):

$$R^2NC \qquad (II),$$

wherein $R^2$ is a substituted or unsubstituted tertiary alkyl group (the compound is referred to as isocyanide (II)), and a base; and adding halfway through the telomerization process a tertiary phosphine represented by the following formula (III):

$$PR^3R^4R^5 \qquad (III),$$

wherein $R^3$, $R^4$ and $R^5$ are each independently an alkyl group having 1 to 10 carbon atoms (the compound is referred to as phosphine (III)).

BEST MODE FOR CARRYING OUT THE INVENTION

The method of the present invention is carried out by initiating telomerization process of a conjugated diene compound in the presence of a hydroxyl compound (I), a palladium compound, an isocyanide (II) and a base, and subsequently adding a phosphine (III).

Specific examples of conjugated diene compounds for use in the present invention include 1,3-butadiene, isoprene, piperylene, 2,3-dimethyl-1,3-butadiene, 1,3,7-octatriene, 1,3-cyclohexadiene and 1,3-cyclooctadiene. These conjugated diene compounds may have a low purity. For example, 1,3-butadiene may be crude butadiene, available at a low costs, composed of 1,3-butadiene and impurities such as butenes (e.g., isobutylene), acetylenes (e.g., methylacetylene and 1-buthyne) and 1,2-butadiene. It is a known fact to those skilled in the art that such crude butadiene can be obtained as a C4 fraction by the thermal cracking of naphtha. The crude butadiene obtained by this way is inexpensive because it is not necessary that 1,3-butadiene is isolated. It is advantageous industrially when the crude butadiene is used as a raw material in the present invention. The method of the present invention for producing ether can utilize low-purity conjugated diene compounds, such as above-mentioned crude butadiene, to achieve high conversion and high selectivity for desired ethers.

The alkyl group represented by $R^1$ in the formula (I) is preferably an alkyl group having 1 to 8 carbon atoms. Examples include methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group and cyclooctyl group. The alkyl group may have substituents, including halogen atoms, such as fluorine atom, chlorine atom, bromine atom and iodine atom; aryl groups, such as phenyl group, tolyl group and xylyl group; alkoxyl groups, such as methoxy group, ethoxy group and isopropoxy group; 2-methoxymethyloxy group and 2-ethoxymethyloxy; and hydroxyl group. The aryl group represented by $R^1$ is preferably an aryl group having 6 to 14 carbon atoms. Examples include phenyl group, naphthyl group, phenanthryl group and anthracenyl group. The aryl group may have substituents, including halogen atoms, such as fluorine atom, chlorine atom, bromine atom and iodine atom; alkyl groups, such as methyl group, ethyl group, propyl group, isopropyl group, butyl group, isobutyl group, s-butyl group, t-butyl group, pentyl group, hexyl group, heptyl group and octyl group; alkoxyl group, such as methoxy group, ethoxy group and isopropoxy group; and hydroxyl group.

Specific examples of the hydroxyl compound (I) include methanol, ethanol, 1-propanol, 2-propanol, 2-methyl-1-propanol, 1-butanol, 2-butanol, pentanol, isopentyl alcohol, cyclopentanol, hexanol, 2-hexanol, cylohexanol, heptanol, octanol, 2-octanol, 3-octanol, benzyl alcohol, phenetyl alcohol, phenol, ethylene glycol, diethylene glycol, propylene glycol, ethylene glycol monomethyl ether, ethylene glycol monoethyl ether, diethylene glycol monomethyl ether, diethylene glycol monoethyl ether, propylene glycol monomethyl ether and propylene glycol monoethyl ether.

The amount of the hydroxyl compound (I) used is preferably in the range of 0.1 to 10 molar equivalents, more preferably in the range of 0.5 to 5 molar equivalents of the conjugated diene compound.

Examples of ethers obtained by the method of the present invention include 1-methoxy-2,7-octadiene, 1-ethoxy-2,7-octadiene, 1-propoxy-2,7-octadiene, 1-butoxy-2,7-octadiene, 1-isopentyloxy-2,7-octadiene, 1-cyclohexyloxy-2,7-octadiene, 1-phenoxy-2,7-octadiene, 1-benzyloxy-2,7-octadiene, 1-methoxy-2,7-dimethyl-2,7-octadiene, 1-ethoxy-2,7-dimethyl-2,7-octadiene, 1-propoxy-2,7-dimethyl-2,7-octadiene, 1-butoxy-2,7-dimethyl-2,7-octadiene, 1-isopentyloxy-2,7-dimethyl-2,7-octadiene, 1-cyclohexyloxy-2,7-dimethyl-2,7-octadiene, 1-phenoxy-2,7-dimethyl-2,7-octadiene, 1-benzyloxy-2,7-dimethyl-2,7-octadiene, 1-methoxy-2,6-dimethyl-2,7-octadiene, 1-ethoxy-2,6-dimethyl-2,7-octadiene, 1-propoxy-2,6-dimethyl-2,7-octadiene, 1-butoxy-2,6-dimethyl-2,7-octadiene, 1-isopentyloxy-2,6-dimethyl-2,7-octadiene, 1-cyclohexyloxy-2,6-dimethyl-2,7-octadiene, 1-phenoxy-2,6-dimethyl-2,7-octadiene, 1-benzyloxy-2,6-dimethyl-2,7-octadiene, 1-methoxy-3,7-dimethyl-2,7-octadiene, 1-ethoxy-3,7-dimethyl-2,7-octadiene, 1-propoxy-3,7-dimethyl-2,7-octadiene, 1-butoxy-3,7-dimethyl-2,7-octadiene, 1-isopentyloxy-3,7-dimethyl-2,7-octadiene, 1-cyclohexyloxy-3,7-dimethyl-2,7-octadiene, 1-phenoxy-3,7-dimethyl-2,7-octadiene, 1-benzyloxy-3,7-dimethyl-2,7-octadiene, 1-methoxy-3,6-dimethyl-2,7-octadiene, 1-ethoxy-3,6-dimethyl-2,7-octadiene, 1-propoxy-3,6-dimethyl-2,7-octadiene, 1-butoxy-3,6-dimethyl-2,7-octadiene, 1-isopentyloxy-3,6-dimethyl-2,7-octadiene, 1-cyclohexyloxy-3,6-dimethyl-2,7-octadiene, 1-phenoxy-3,6-dimethyl-2,7-octadiene, 1-benzyloxy-3,6-dimethyl-2,7-octadiene, 3-methoxy-2,7-octadiene, 3-ethoxy-2,7-octadiene, 3-propoxy-2,7-octadiene, 3-butoxy-2,7-octadiene, 3-isopentyloxy-2,7-octadiene, 3-cyclohexyloxy-2,7-octadiene, 3-phenoxy-2,7-octadiene, 3-benzyloxy-2,7-octadiene, 3-methoxy-2,7-dimethyl-2,7-octadiene, 3-ethoxy-2,7-dimethyl-2,7-octadiene, 3-propoxy-2,7-dimethyl-2,7-octadiene, 3-butoxy-2,7-dimethyl-2,7-octadiene, 3-isopentyloxy-2,7-dimethyl-2,7-octadiene, 3-cyclohexyloxy-2,7-dimethyl-2,7-octadiene, 3-phenoxy-2,7-dimethyl-2,7-octadiene, 3-benzyloxy-2,7-dimethyl-2,7-octadiene, 3-methoxy-2,6-dimethyl-2,7-octadiene, 3-ethoxy-2,6-dimethyl-2,7-octadiene, 3-propoxy-2,6-dimethyl-2,7-octadiene, 3-butoxy-2,6-dimethyl-2,7-octadiene, 3-isopentyloxy-2,6-dimethyl-2,7-octadiene, 3-cyclohexyloxy-2,6-dimethyl-2,7-octadiene, 3-phenoxy-2,6-dimethyl-2,7-octadiene, 3-benzyloxy-2,6-dimethyl-2,7-octadiene, 3-methoxy-3,7-dimethyl-2,7-octadiene, 3-ethoxy-3,7-dimethyl-2,7-octadiene, 3-propoxy-3,7-dimethyl-2,7-octadiene, 3-butoxy-3,7-dimethyl-2,7-octadiene, 3-isopentyloxy-3,7-dimethyl-2,7-octadiene, 3-cyclohexyloxy-3,7-dimethyl-2,7-octadiene, 3-phenoxy-3,7-dimethyl-2,7-octadiene, 3-benzyloxy-3,7-dimethyl-2,7-octadiene, 3-methoxy-3,6-dimethyl-2,7-octadiene, 3-ethoxy-3,6-dimethyl-2,7-octadiene, 3-propoxy-3,6-dimethyl-2,7-octadiene, 3-butoxy-3,6-dimethyl-2,7-octadiene, 3-isopentyloxy-3,6-dimethyl-2,7-octadiene, 3-cyclohexyloxy-3,6-dimethyl-2,7-octadiene, 3-phenoxy-3,6-dimethyl-2,7-octadiene, 2,7-octadiene and 3-benzyloxy-3,6-dimethyl-2,7-octadiene.

The palladium compound for use in the present invention may be any palladium compound that does not contain the compounds having a phosphorus atom. Examples include palladium formate, palladium acetate, palladium chloride, palladium bromide, palladium carbonate, palladium sulfate, palladium nitrate, sodium palladium chloride, potassium palladium chloride, palladium acetylacetonate, bis(benzonitrile) palladium dichloride, bis(t-butylisocyanide)palladium dichloride, bis(dibenzylideneacetone)palladium, tris(dibenzylideneacetone)dipalladium and bis(1,5-cyclooctadiene) palladium. Of these, palladium acetate and palladium acetylacetonate are particularly preferred because of their availability and cost efficiency. The amount of the palladium compound used is in the range of 0.1 ppm to 100 ppm, more preferably in the range of 1 ppm to 50 ppm (as determined by the amount of palladium atoms), relative to 1 mol of the conjugated diene compound.

Examples of the substituted or unsubstituted tertiary alkyl group represented by $R^2$ in the formula (II) include t-butyl group, 1,1-dimethylhexyl group, trityl group and 1-methylcyclohexyl group.

Specific Examples of the isocyanide (II) for use in the present invention include t-butyl isocyanide, t-octyl isocyanide, trityl isocyanide and 1-methylcyclohexyl isocyanide. Of these, t-butyl isocyanide and t-octyl isocyanide are particularly preferred because of their availability and cost efficiency. Unlike tertiary isocyanides, primary or secondary isocyanides are not used in the method of the present invention because the hydrogen atoms on the alpha-carbon of primary or secondary isocyanides are pulled out by the base used in the method of the present invention, causing the isocyanides to decompose and thus terminating the reaction.

The amount of the isocyanide (II) used is preferably in the range of 1 to 50 mol, more preferably in the range of 1 to 20 mol, for each 1 mol of palladium atoms present in the palladium compound.

The base for use in the present invention may be a compound represented by the following formula (IV):

wherein M is an alkali metal or alkaline earth metal; $R^6$ is a hydrogen atom, a substituted or unsubstituted alkyl group or a substituted or unsubstituted aryl group; and n is 1 when M is an alkali metal or 2 when M is an alkaline earth metal, a compound represented by the following formula (V):

wherein $R^7$, $R^8$, $R^9$, $R^{10}$ and $R^{11}$ are each independently a hydrogen atom, a substituted or unsubstituted alkyl group, or a substituted or unsubstituted aryl group, or a compound represented by the formula (VI):

wherein $R^{12}$, $R^{13}$, $R^{14}$, $R^{15}$ and $R^{16}$ are each independently a hydrogen atom, a substituted or unsubstituted alkyl group, or a substituted or unsubstituted aryl group.

Examples of the alkyl group represented by $R^6$, $R^7$, $R^8$, $R^9$, $R^{10}$, $R^{11}$, $R^{12}$, $R^{13}$, $R^{14}$, $R^{15}$, $R^{16}$ in the formulas (IV), (V) and (VI) include methyl group, ethyl group, propyl group, isopropyl group, butyl group, isobutyl group, s-butyl group, t-butyl group, pentyl group, hexyl group, heptyl group, octyl group, cyclopentyl group, cyclohexyl group, cycloheptyl group and cyclooctyl group. Examples of the aryl group include phenyl group and naphthyl group. These groups may have substituents, including phenyl groups, such as phenyl group, tolyl group and xylyl group.

Specific examples of the compound of the formula (IV) include alkali metal hydroxides, such as lithium hydroxide, sodium hydroxide and potassium hydroxide; alkaline earth metal hydroxides, such as calcium hydroxide, magnesium hydroxide and barium hydroxide; lithium methoxide, sodium methoxide, sodium isopropoxide, sodium s-butoxide, sodium phenoxide, sodium benzyloxide, potassium methoxide, potassium ethoxide, potassium isopropoxide, potassium s-butoxide, potassium t-butoxide, potassium phenoxide, potassium benzyloxide, magnesium methoxide, magnesium ethoxide, magnesium isopropoxide, magnesium s-butoxide, magnesium t-butoxide, magnesium phenoxide, magnesium benzyloxide, calcium methoxide, calcium ethoxide, calcium isopropoxide, calcium s-butoxide, calcium t-butoxide, calcium phenoxide and calcium benzyloxide.

Specific examples of the compound of the formula (V) include tetramethylammonium hydroxide, tetraethylammonium hydroxide, tetra-n-propylammonium hydroxide, triisopropylammonium hydroxide, tetra-n-butylammonium hydroxide, benzyltrimethylammonium hydroxide, tetramethylammonium methoxide, tetramethylammonium ethoxide, tetramethylammonium n-propoxide, tetramethylammonium phenoxide, tetraethylammonium methoxide, tetraethylammonium ethoxide, tetraethylammonium propoxide, tetraethylammonium phenoxide, tetra-n-propylammonium methoxide, tetra-n-propylammonium ethoxide, triisopropylammonium methoxide, triisopropylammonium ethoxide, tetra-n-butylammonium methoxide, tetra-n-butylammonium ethoxide, tetra-n-butylammonium phenoxide, benzyltrimethylammonium methoxide, benzyltrimethylammonium ethoxide and benzyltrimethylammonium phenoxide.

Specific examples of the compound of the formula (VI) include tetramethylphosphonium hydroxide, tetraethylphosphonium hydroxide, tetra-n-propylphosphonium hydroxide, triisopropylphosphonium hydroxide, tetra-n-butylphosphonium hydroxide, benzyltrimethylphosphonium hydroxide, tetraphenylphosphonium hydroxide, tetramethylphosphonium methoxide, tetraethylphosphonium methoxide, tetra-n-propylphosphonium methoxide, triisopropylphosphonium methoxide, tetra-n-butylphosphonium methoxide, tetra-n-butylphosphonium ethoxide, tetra-n-butylphosphonium phenoxide, benzyltrimethylphosphonium ethoxide, tetraphenylphosphonium methoxide, tetraphenylphosphonium ethoxide and tetraphenylphosphonium phenoxide.

The amount of the base used is preferably in the range of 0.1 to 10000 mol, more preferably in the range of 1 to 3000 mol, for each 1 mol of palladium atoms present in the palladium compound.

The method of the present invention can be carried out either in the presence of solvents or in the absence of solvents. Examples of such solvents include hydrocarbons, such as butane, isobutane, butene, isobutene, pentane, hexane, cyclohexane, benzene, toluene and xylene; halogenated hydrocarbons, such as dichloromethane, 1,2-dichloroethane and chloroform; ethers, such as tetrahydrofuran, dipentyl ether, dihexyl ether, diethylene glycol dimethyl ether, triethylene glycol dimethyl ether and tetraethylene glycol dimethyl ether; and amides, such as formamide, acetamide, N,N-dimethylformamide and 1-methyl-2-pyrrolidinone. These solvents may be used either individually or in combination of two or more. When the method is carried out in the presence of a solvent, the amount of the solvent used is typically in the range of 0.01 to 10 times the mass of the conjugated diene compound.

The method of the present invention is preferably carried out at a temperature of 0 to 150° C., and more preferably at a temperature of 20 to 110° C. The reaction rate tends to be significantly decreased below 0° C., whereas increased amounts of by-products tend to result above 150° C.

The method is preferably carried out under a pressure of 0.1 to 3 MPa.

The method is preferably carried out under inert gas atmosphere, such as nitrogen and argon.

In the method of the present invention, the phosphine (III) is added to the reaction mixture halfway through the telomerization process, preferably when the conversion of the conjugated diene compound reaches 35%, more preferably 50%, and still more preferably 70%. This keeps the reaction rate from decreasing as the concentration of the remaining conjugated diene compound decreases or this even increases the reaction rate. As a result, more conjugated diene compound in the reaction system is converted. The method of the present invention is particularly advantageous in that it can achieve high conversion of a conjugated diene compound when low-purity conjugated diene compounds, such as the 'crude butadiene', are used in the process also. The method of the present invention has achieved an increase in both the conversion and the selectivity by adding the phosphine (III) halfway through the telomerization process, not at the beginning of the process.

Increasing the temperature by 1 to 10° C. following the addition of the phosphine (III) may further facilitate the reaction.

The conversion of the conjugated diene compound can be determined by subjecting a portion of the reaction mixture to gas chromatography analysis, as described later.

Examples of the alkyl group represented by $R^3$, $R^4$ or $R^5$ in the formula (III) include methyl group, ethyl group, n-propyl group, isopropyl group, n-butyl group, isobutyl group, t-butyl group, n-heptyl group, n-octyl group, n-nonyl group and n-decyl group.

Specific examples of the phosphine (III) include trimethylphosphine, triethylphosphine, tripropylphosphine, triisopropylphosphine, tributylphosphine, triisobutylphosphine, triisopentylphosphine, trihexylphosphine, tricyclohexylphosphine, trioctylphosphine and tridecylphosphine. The amount of the phosphine (III) used is preferably in the range of 0.01 to 100 mol, more preferably in the range of 0.05 to 10 mol, and still more preferably in the range of 0.1 to 5 mol for each 1 mol of palladium atoms present in the palladium compound. The phosphine present in amounts less than 0.01 mol for each 1 mol of palladium atoms cannot improve the reaction rate, while the phosphine present in amounts exceeding 100 mol for each 1 mol of palladium atoms cannot provide correspondingly enhanced effect but adds to the production cost.

In the method of the present invention, water may be added to the reaction mixture when the phosphine (III) is added to the reaction mixture. The addition of water prevents the decrease in the selectivity caused by simultaneous coordination of the phosphine (III) and the isocyanide (II).

When water is added to the reaction mixture, the amount of water added is preferably in the range of 10 to 10000 mol, more preferably in the range of 20 to 5000 mol, and in the viewpoint of the reaction rate still more preferably in the range of 50 to 2000 mol for each 1 mol of palladium atoms present in the palladium compound.

In the method of the present invention, the phosphine (III) and water may each be added in any suitable manner: Each may be added to the reaction mixture directly, or each may be diluted with the hydroxyl compound (I) and/or the above-described solvent prior to addition to the reaction mixture.

Although the reaction time may vary depending on the type and amount of the hydroxyl compound (I), the conjugated diene compound, the isocyanide (II), the palladium compound, the base and the phosphine (III), as well as on the reaction temperature and reaction pressure, it takes for the reaction is typically in the range of 0.5 to 10 hours prior to the addition of the phosphine (III) and in the range of 0.5 to 10 hours following the addition of the phosphine (III).

The method of the present invention may be carried out in any suitable manner, for example, a batch process or a continuous process. When the manner is a continuous process, a piston flow reactor, a continuous stirred tank reactor or combination of these reactors may be used.

In a typical batch process, the hydroxyl compound (I), the base, the palladium compound, the isocyanide (II) and, optionally, the solvent are added together under nitrogen atmosphere. To the resulting mixture, the conjugated diene compound is added and the reaction is allowed to proceed at a specific temperature under a specific pressure over a specific period of time. Subsequently, the phosphine (III) and optional water are added and the reaction is further carried out for a specific period of time.

In a typical continuous process, the hydroxyl compound (I), the base, the palladium compound, the isocyanide (II) and, optionally, the solvent are added together under nitrogen atmosphere. To the resulting mixture, a predetermined amount of the conjugated diene compound is added. The mixture is continuously or intermittently transferred to a first tank, where the reaction is allowed to proceed for a specific period of time. Subsequently, the reaction mixture is discharged from the first tank either continuously or intermittently. To the mixture, the phosphine (III) and optional water are added and the resulting mixture is continuously or intermittently transferred to a second tank, where the reaction is allowed to further proceed for a specific period of time.

Upon completion of the reaction, ethers are separated from the reaction mixture using techniques commonly used in the separation/purification of organic compounds. In one exemplary separation/purification process, unreacted starting materials and the optional solvent are evaporated and, if necessary, the catalysts are separated from the residue using such techniques as thin film distillation, decantation, extraction and adsorption. The resulting residue is then purified by distillation, recrystallization or column chlomatography to give highly pure ethers.

EXAMPLES

The present invention will now be described in further detail with reference to examples, which are not intended to limit the scope of the invention in any way. In Examples and Comparative Examples that follow, gas chromatography analysis was conducted in the manner described below.

—Gas Chromatography Analysis—

Instrument: GC-14B (manufactured by Shimadzu)

Column: DB-WAX (10 m) (manufactured by Agilent Technologies)

Analytical conditions: injection temp.=220° C.; detection temp.=250° C.; temperature kept at 40° C. for 8 min, increased at a rate of 15° C./min to 240° C., and kept at 240° C. for 30 min.

A 'crude butadiene' having the following composition was used in Examples and Comparative Examples:

—Composition of Crude Butadiene—

1,3-butadiene: 41.1 mass %, 1,2-butadiene: 0.3 mass %, butenes: 43.0 mass %, butanes: 10.3 mass %, acetylenes: 0.04 mass %, other components: 5.26 mass %.

Example 1

Methanol (23.7 g, 0.74 mol), sodium methoxide (12.8 mg, 0.24 mmol), t-butylisocyanide (0.98 mg, 0.012 mmol) and palladium acetylacetonate (0.72 mg, 0.0024 mmol) were added and dissolved together in a 100 ml three-necked flask under nitrogen atmosphere. The mixture was placed in a 100 ml autoclave equipped with a stirrer under nitrogen atmosphere. Pressurized liquid 1,3-butadiene (30 mL, 18.9 g, 0.35 mol) was then fed to the autoclave. While stirred, the mixture was heated to 100° C. and was continuously stirred at this temperature for 3 hours. The gas chromatography analysis of the reaction mixture showed that the conversion of 1,3-butadiene was 74%, at this point. Subsequently, triethylphosphine (0.56 g, 0.0047 mmol), water (42.6 mg, 2.4 mmol) and methanol (2.37 g, 0.074 mol) were added and the mixture was stirred for another 3 hours while kept at 100° C.

A small portion of the reaction mixture was taken and was analyzed by the gas chromatography analysis. The result showed that the conversion of 1,3-butadiene was 98%, the selectivity for 1-methoxy-2,7-octadiene was 88.1%, the selectivity for 3-methoxy-1,7-octadiene was 5.9% and the combined selectivity for vinylcyclohexene and 1,3,7-octatriene was 3% or less.

Example 2

The process and analyses were conducted in the same manner as in Example 1, except that tributylphosphine (0.95 g, 0.0047 mmol) was used, rather than triethylphosphine (0.56 g, 0.0047 mmol). The result showed that the conversion of 1,3-butadiene was 98%, the selectivity for 1-methoxy-2,7-octadiene was 87.8%, the selectivity for 3-methoxy-1,7-octadiene was 6.3% and the combined selectivity for vinylcyclohexene and 1,3,7-octatriene was 3% or less.

Example 3

The process and analyses were conducted in the same manner as in Example 1, except that triethylphosphine (0.56 g, 0.0047 mmol) and methanol (3.0 mL, 2.37 g) were used, rather than triethylphosphine (0.56 g, 0.0047 mmol), water (42.6 mg, 2.4 mmol) and methanol (3.0 mL, 2.37 g). The result showed that the conversion of 1,3-butadiene was 98%, the selectivity for 1-methoxy-2,7-octadiene was 87.5%, the selectivity to 3-methoxy-1,7-octadiene was 10.5% and the combined selectivity for vinylcyclohexene and 1,3,7-octatriene was 2% or less.

Example 4

The process and analyses were conducted in the same manner as in Example 1, except that water was increased from 42.6 mg (2.4 mmol) to 85.2 mg (4.8 mmol). The result showed that the conversion of 1,3-butadiene was 99%, the selectivity for 1-methoxy-2,7-octadiene was 90.3%, the selectivity for 3-methoxy-1,7-octadiene was 5.1% and the combined selectivity for vinylcyclohexene and 1,3,7-octatriene was 3% or less.

Example 5

Methanol (23.7 g, 0.74 mol), sodium methoxide (12.8 mg, 0.24 mmol), t-butylisocyanide (0.98 mg, 0.012 mmol) and palladium acetylacetonate (0.72 mg, 0.0024 mmol) were added and dissolved together in a 100 ml three-necked flask under nitrogen atmosphere. The mixture was placed in a 100 mL autoclave equipped with a stirrer under nitrogen atmosphere. 77 mL of pressurized liquid 'crude butadiene' (equivalent to 18.9 g (0.35 mol) of 1,3-butadiene) was then fed to the autoclave. While stirred, the mixture was heated to 100° C. and was continuously stirred at this temperature for 3 hours. The gas chromatography analysis of the reaction mixture showed that the conversion of 1,3-butadiene was 52%, at this point. Subsequently, triethylphosphine (0.56 g, 0.0047 mmol), water (42.6 mg, 2.4 mmol) and methanol (2.37 g, 0.074 mol) were added and the mixture was stirred for another 3 hours while kept at 100° C.

A small portion of the reaction mixture was taken and was analyzed by the gas chromatography analysis. The result showed that the conversion of 1,3-butadiene was 98%, the selectivity for 1-methoxy-2,7-octadiene was 89.1%, the selectivity for 3-methoxy-1,7-octadiene was 6.1% and the combined selectivity for vinylcyclohexene and 1,3,7-octatriene was 3% or less.

Comparative Example 1

Methanol (23.7 g, 0.74 mol), sodium methoxide (12.8 mg, 0.24 mmol), t-butylisocyanide (0.98 mg, 0.012 mmol), palladium acetylacetonate (0.72 mg, 0.0024 mmol) and triethylphosphine (0.56 g, 0.0047 mmol) were added together under 100 mL autoclave under nitrogen atmosphere. Pressurized 1,3-butadiene (30 mL, 18.9 g, 0.35 mol) was then added. While stirred, the mixture was heated to 100° C. and was continuously stirred at this temperature for 3 hours. A small portion of the reaction mixture was taken and was analyzed by the gas chromatography analysis. The result showed that the conversion of 1,3-butadiene was 98%, the selectivity for 1-methoxy-2,7-octadiene was 59.4%, the selectivity for 3-methoxy-1,7-octadiene was 34.7% and the combined selectivity for vinylcyclohexene and 1,3,7-octatriene was 3% or less.

Comparative Example 2

Methanol (23.7 g, 0.74 mol), sodium methoxide (12.8 mg, 0.24 mmol), t-butylisocyanide (0.98 mg, 0.012 mmol) and palladium acetylacetonate (0.72 mg, 0.0024 mmol) were added and dissolved together in a 100 ml three-necked flask under nitrogen atmosphere. The mixture was placed in a 100 mL autoclave equipped with a stirrer under a nitrogen atmosphere. 77 mL of pressurized liquid 'crude butadiene' (equivalent to 18.9 g (0.35 mol) of 1,3-butadiene) was then fed to the autoclave. While stirred, the mixture was heated to 100° C. and was continuously stirred at this temperature for 6 hours.

A small portion of the reaction mixture was taken and was analyzed by the gas chromatography analysis. The result showed that the conversion of 1,3-butadiene present in the crude butadiene was 48%, the selectivity for 1-methoxy-2,7-octadiene was 90.1%, the selectivity for 3-methoxy-1,7-octadiene was 3.1% and the combined selectivity for vinylcyclohexene and 1,3,7-octatriene was 3% or less.

The results of Examples 1-4 and Comparative Example 1 indicate that the selectivity for the purpose compound is low when the isocyanate (II) and the phosphine (III) are added together at the beginning of the process whereas the selectivity is considerably high when the method of the present invention is used. The results of Example 5 and Comparative Example 2 indicate that when a 'crude butadiene' is used as a raw material, adding the phosphine (III) halfway through the telomerization process significantly increases the conversion of 1,3-butadiene (Example 5) as compared to phosphine-free process (Comparative Example 2) as well as the reaction rate.

The invention claimed is:

1. A method for producing an ether, comprising the steps of:

initiating telomerization process of a conjugated diene compound with an hydroxyl compound represented by the following formula (I):

$$R^1OH \qquad (I),$$

wherein $R^1$ is a substituted or unsubstituted alkyl or aryl group, in the presence of a palladium compound, a tertiary isocyanide represented by the following formula (II):

$$R^2NC \tag{II}$$

wherein $R^2$ is a substituted or unsubstituted tertiary alkyl group, and a base; and adding halfway through the telomerization process a tertiary phosphine represented by the following formula (III):

$$PR^3R^4R^5 \tag{III}$$

wherein $R^3$, $R^4$ and $R^5$ are each independently an alkyl group having 1 to 10 carbon atoms.

2. The method for producing an ether according to claim 1, wherein the tertiary phosphine is added when the conversion of the conjugated diene compound reaches 35% or higher.

3. The method for producing an ether according to claim 1, wherein the conjugated diene compound is 1,3-butadiene or isoprene.

4. The method for producing an ether according to claim 1, wherein the conjugated diene compound is a crude butadiene.

5. The method for producing an ether according to claim 1, wherein water is added along with the tertiary phosphine.

* * * * *